United States Patent
Howell et al.

[11] Patent Number: 6,139,532
[45] Date of Patent: Oct. 31, 2000

[54] CLAMPING WING FOR CATHETER INTRODUCER

[75] Inventors: Glade H. Howell, Sandy; Steven Wayne Johnson, West Jordan, both of Utah

[73] Assignee: Becton, Dickinson and Company, Franklin Lakes, N.J.

[21] Appl. No.: 09/153,662

[22] Filed: Sep. 15, 1998

[51] Int. Cl.[7] .......................... A61M 5/178; A61M 5/32
[52] U.S. Cl. .......................................... 604/165; 604/177
[58] Field of Search ................................... 604/164, 165, 604/168, 174, 177, 264, 272, 528, 533

[56] References Cited

U.S. PATENT DOCUMENTS

| | | | |
|---|---|---|---|
| 3,589,361 | 6/1971 | Loper et al. | 128/214.4 |
| 3,769,975 | 11/1973 | Nimoy et al. | 128/214.4 |
| 3,786,810 | 1/1974 | Pannier, Jr. et al. | 128/214.4 |
| 4,177,809 | 12/1979 | Moorehead | 128/214.4 |
| 4,192,305 | 3/1980 | Seberg | 128/214.4 |
| 4,192,306 | 3/1980 | Genese | 128/214.4 |
| 4,194,504 | 3/1980 | Harms et al. | 128/214.4 |
| 4,300,553 | 11/1981 | Seberg | 128/214.4 |
| 4,362,156 | 12/1982 | Feller, Jr. et al. | 604/165 |
| 4,388,074 | 6/1983 | Seberg et al. | 604/165 |
| 4,389,210 | 6/1983 | Genese | 604/177 |
| 4,632,670 | 12/1986 | Mueller, Jr. | 604/174 |
| 4,728,322 | 3/1988 | Walker et al. | 604/165 |
| 4,840,613 | 6/1989 | Balbierz | 604/51 |
| 5,112,312 | 5/1992 | Luther | 604/177 |
| 5,163,913 | 11/1992 | Rantanen-Lee et al. | 604/177 |
| 5,257,980 | 11/1993 | Van Antwerp et al. | 604/282 |
| 5,306,253 | 4/1994 | Brimhall | 604/165 |
| 5,385,554 | 1/1995 | Brimhall | 604/168 |
| 5,814,021 | 9/1998 | Balbierz | 604/174 |

FOREIGN PATENT DOCUMENTS

| | | | |
|---|---|---|---|
| 0 567 029 | 10/1993 | European Pat. Off. | A61M 25/02 |
| 1131865 | 10/1968 | United Kingdom | A61M 25/00 |

*Primary Examiner*—Glenn K. Dawson
*Assistant Examiner*—Michael J. Hayes
*Attorney, Agent, or Firm*—Eric M. Lee

[57] ABSTRACT

A winged catheter introducer for use in introducing a catheter into a blood vessel is disclosed. A needle is disposed within the catheter to help penetrate a patient's blood vessel. The needle and catheter are disposed within an introducer body having a pair of deformable wings extending from opposite sides of the body. A pair of opposing clamp jaws are disposed within the introducer body adjacent the wings. The clamp jaws are configured to grip and retain the catheter and needle when the wings are compressed towards each other. In a disclosed embodiment, the clamp jaws are biased in an open configuration and define clamp surfaces having angled ridges which engage the catheter exterior surface.

18 Claims, 5 Drawing Sheets

CLAMPING WING FOR CATHETER INTRODUCER

FIELD OF THE INVENTION

The present invention relates to a winged catheter introducer useful for inserting a catheter into a living subject. More particularly, the present invention relates to a winged catheter introducer configured to securely clamp the catheter and insertion needle when the wings are pinched between the practitioner's forefinger and thumb.

BACKGROUND

Winged catheter introducers are commonly used by the medical profession to introduce a flexible catheter into a patient's blood vessel. Examples of typical winged catheter introducers are found in U.S. Pat. Nos. 4,177,809, 5,163,913, and 5,306,253, which are incorporated herein by reference. Winged catheter introducers typically include a flexible catheter attached to a winged member and a translucent tube. Inside the catheter is a needle with a wire attached to it. The needle aids in the insertion of the catheter into a blood vessel, and it is withdrawn by pulling the wire once the catheter has been successfully introduced into the vessel.

In use, the wings are gripped between the practitioner's forefinger and thumb. The wings are bent towards each other and squeezed. This squeezing action causes the winged member to impinge on the needle and flexible catheter, thereby gripping the needle and catheter. It is important that the needle and catheter are securely gripped because the practitioner uses the needle to pierce the skin in the vicinity of the vessel to which access is desired. If the needle slips or moves during insertion, the appropriate vessel may not be penetrated. Tissue damage and unnecessary harm to the patient may result.

When the vessel is penetrated, the blood pressure in the vessel will cause blood to flow up the needle bore and into the translucent tubing. The practitioner verifies the penetration of the vessel by looking for blood "flashback" in the tubing. The needle is withdrawn from the catheter, and the catheter is preferably advanced within the blood vessel to a desired position.

It will be appreciated that there is a continuing need in the art for a winged catheter introducer which securely clamps and stabilizes the needle and catheter when the wings are pinched.

Such winged catheter introducer is disclosed and claimed herein.

SUMMARY OF THE INVENTION

The present invention is directed to a winged catheter introducer having a clamp structure for securely clamping the catheter and insertion needle when the wings are pinched between the practitioner's forefinger and thumb. In one embodiment, the winged catheter introducer includes a catheter for introduction into a blood vessel and an insertion needle. The catheter has an exterior surface and an interior surface. The needle has a sharp tip at its distal end for piercing a patient's skin and blood vessel. The needle is partially disposed within the catheter such that the sharp tip extends from the distal end of the catheter. A thin wire is preferably attached to the proximal end of the needle so that the needle can be removed from the catheter after the catheter is properly positioned within the patient.

The winged catheter introducer includes an introducer body having an introducer lumen extending therethrough and having a pair of wings extending laterally from the body. The catheter and insertion needle are disposed within the introducer lumen. As with conventional winged catheter introducers, the wings are deformable from a relaxed position, where the wings extend laterally from the body, to a compressed position, where the wings are pinched together between the practitioner's forefinger and thumb.

The present invention provides at least one clamp jaw and preferably a pair of opposing clamp jaws disposed within the introducer lumen adjacent the wings. The clamp jaws are configured to grip and retain the catheter and needle when the wings are in the compressed position. In a presently preferred embodiment, the clamp jaws are biased in an open configuration when the wings are in the relaxed position. In the open configuration, the catheter and needle can slide between the clamp jaws within the introducer lumen. The clamp jaws each define a clamp surface which engages the catheter exterior surface.

In a presently preferred embodiment, each clamp surface contains at least one angled ridge which engages the catheter exterior surface. The angled ridges preferably engage the catheter exterior surface in a direction transverse to the longitudinal axis of the catheter. Other angled ridge configurations for engaging the catheter exterior surface can be used, such as a crisscross or herringbone arrangement.

The clamp surface ridges are preferably offset so that they do not directly oppose each other. Also, the ridges preferably are sharply tapered on one side of the ridge and gradually tapered on the other side of the ridge. This allows for greater gripping force in one longitudinal direction than another.

The insertion needle is preferably hollow, having a sharp beveled tip at its distal end and configured to allow blood flashback to provide a visual indication of blood vessel penetration. In a currently preferred embodiment, the needle has a roughened exterior surface to facilitate gripping contact between the interior surface of the catheter and the exterior surface of the needle.

DESCRIPTION OF THE INVENTION

Figure 1:
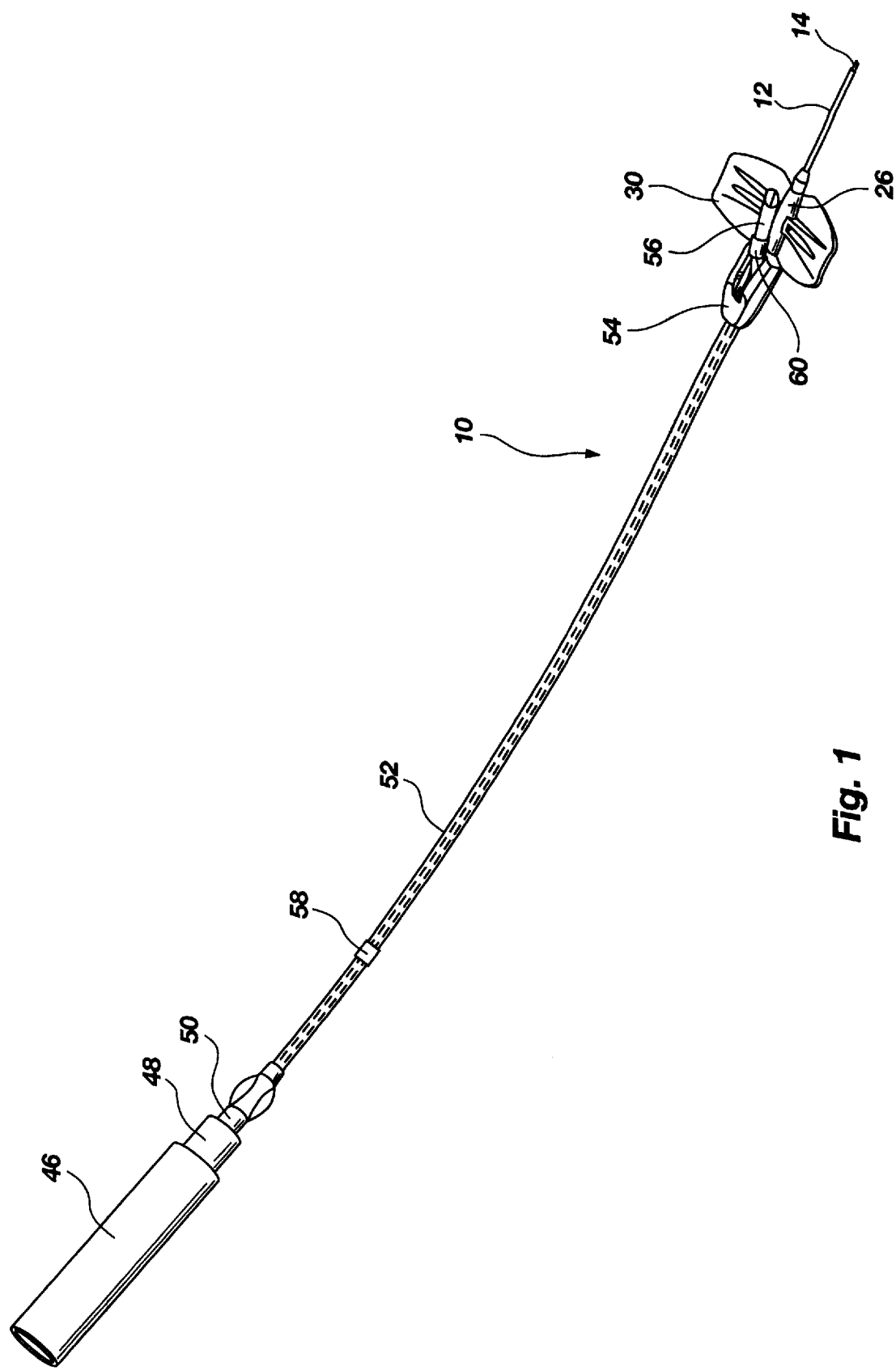
FIG. 1 is a perspective view of a winged catheter introducer assembly within the scope of the present invention.
Figure 2:
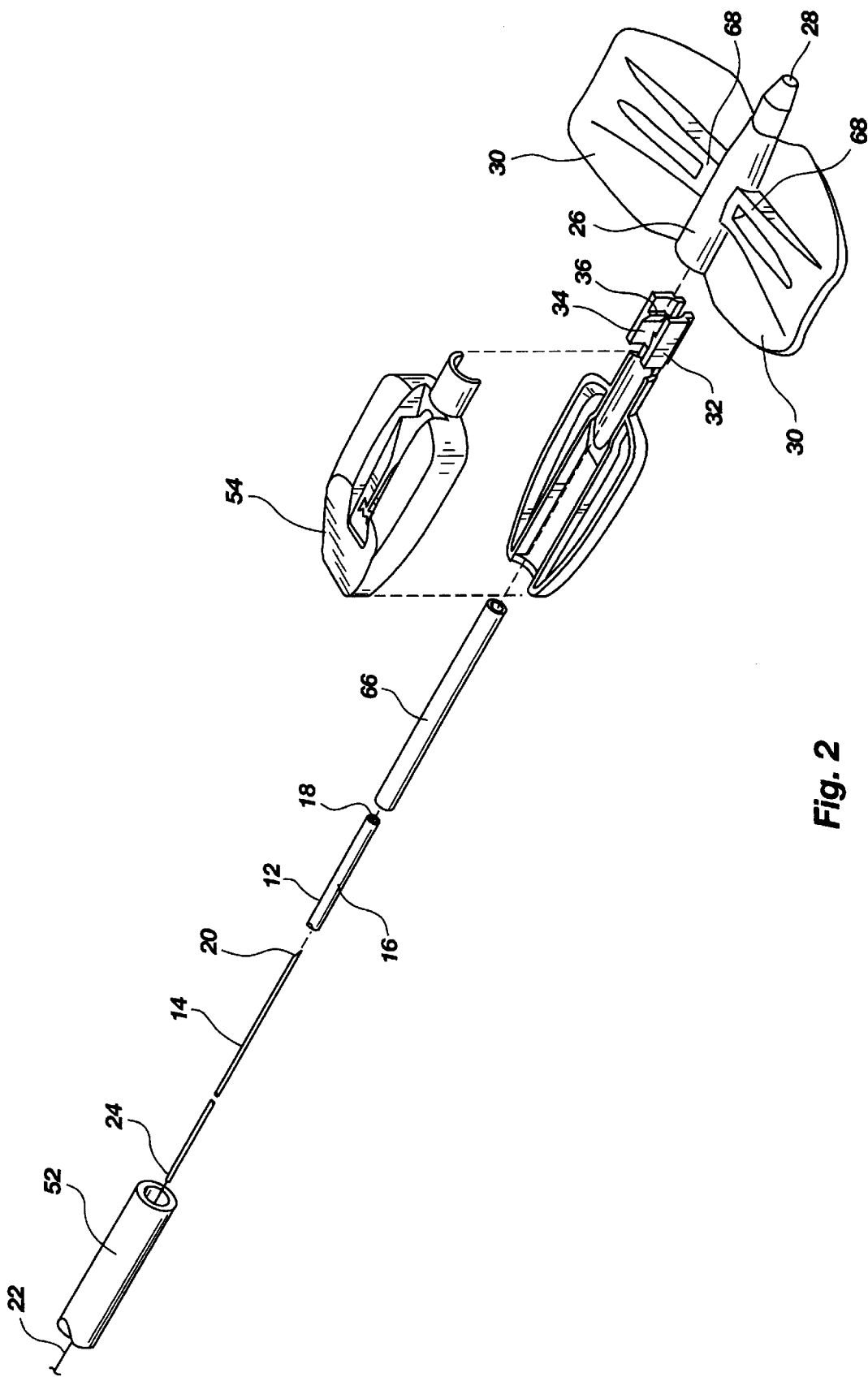
FIG. 2 is an enlarged, exploded perspective view of various parts assembled to form the catheter introducer assembly of FIG. 1.

The present invention will now be described with reference to the figures. FIGS. 1 and 2 show one embodiment of a winged catheter introducer assembly 10 within the scope of the present invention. The winged catheter introducer assembly 10 includes a catheter 12 for introduction into a blood vessel and an insertion needle 14. The catheter 12 has a catheter lumen defining a catheter exterior surface 16 and a catheter interior surface 18. The needle 14 has a sharp tip 20 at its distal end for piercing a patient's skin and blood vessel. The needle 14 is preferably partially disposed within the catheter lumen such that the sharp tip 20 extends from the distal end of catheter 12, as shown best in FIG. 3. A thin wire 22 is preferably attached to the proximal end 24 of the needle so that the needle can be removed from the catheter 12 after the catheter is properly positioned within the patient.

Figure 4:
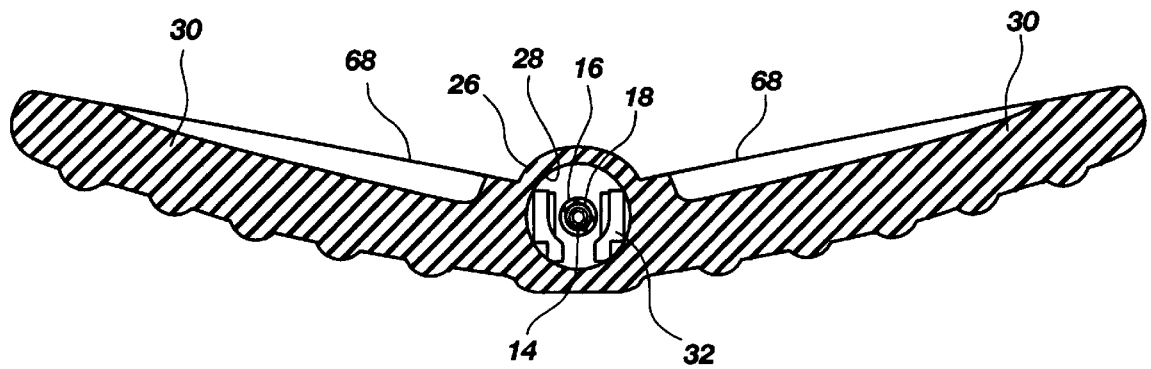
FIG. 4 is an enlarged, transverse cross-sectional view of the catheter introducer assembly in which the catheter introducer wings are in a relaxed position.
Figure 5:
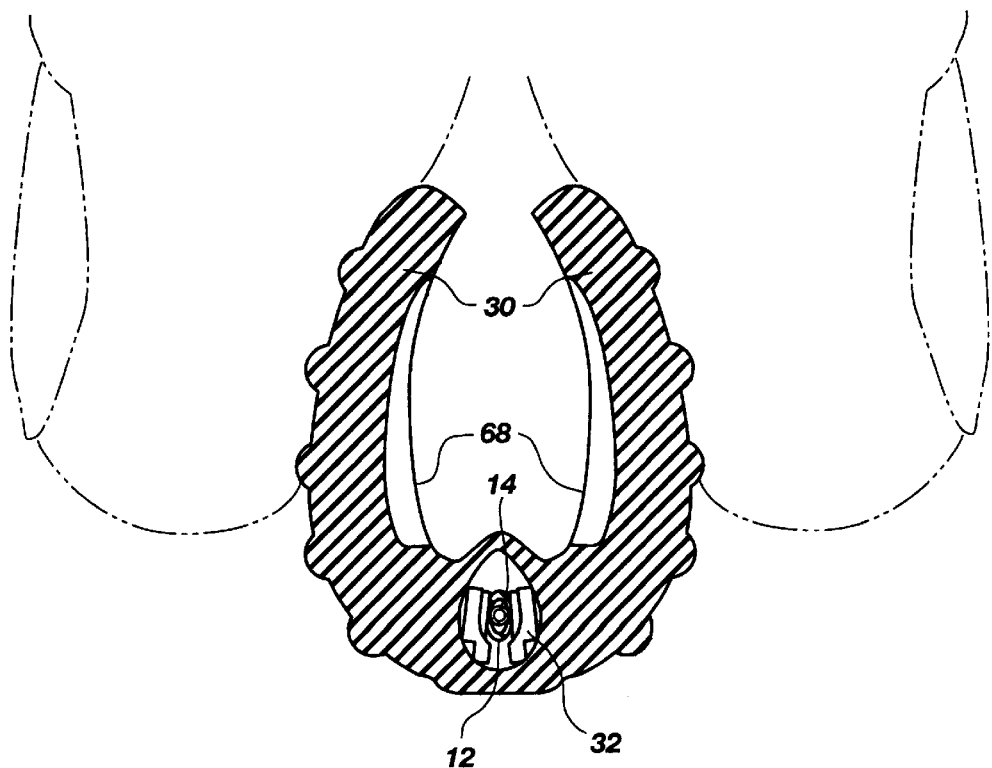
FIG. 5 is an enlarged, transverse cross-sectional view of the catheter introducer assembly in which the catheter introducer wings are in a compressed position.

The winged catheter introducer assembly 10 includes an introducer body 26 having an introducer lumen 28 extending therethrough, shown best in FIGS. 4 and 5. A pair of wings 30 extend from opposite sides of the body 26. The catheter 12 and insertion needle 14 are initially disposed within the introducer lumen 28. As with conventional winged catheter introducers, the wings 30 are deformable from a relaxed position, shown in FIG. 4, where the wings 30 extend laterally from the body 26, to a compressed position, shown in FIG. 5, where the wings 30 are pinched together between the practitioner's forefinger and thumb. The wings 30 are preferably in a pre-bent configuration as disclosed in U.S. Pat. No. 5,306,253.

The present invention is unique in providing at least one clamp jaw and preferably a pair of opposing clamp jaws 32 disposed within the introducer lumen 26 adjacent the wings 30. The clamp jaws 32 are configured to grip and retain the catheter 12 and needle 14 when the wings 30 are in the compressed position. In a presently preferred embodiment, the clamp jaws 32 are biased in an open configuration when the wings 30 are in the relaxed position. In the open configuration, the catheter 12 and needle 14 can slide between the clamp jaws 32 within the introducer lumen 26. The clamp jaws 32 each define a clamp surface 34 which engages the catheter exterior surface 16.

In a presently preferred embodiment, each clamp surface 34 contains at least one angled ridge 36 which engages the catheter exterior surface 16. The angled ridges 36 preferably transversely engage the catheter exterior surface 16. As used herein, the ridges transversely engage the catheter 12 in a direction which is not parallel to the catheter longitudinal axis. In a preferred embodiment, the ridges 36 engage the catheter 12 across the catheter exterior surface 16 at a right angle relative to the longitudinal axis of the catheter. Other configurations for engaging the catheter exterior surface are within the scope of the present invention, including a crisscross or herringbone arrangement.

Figure 3:
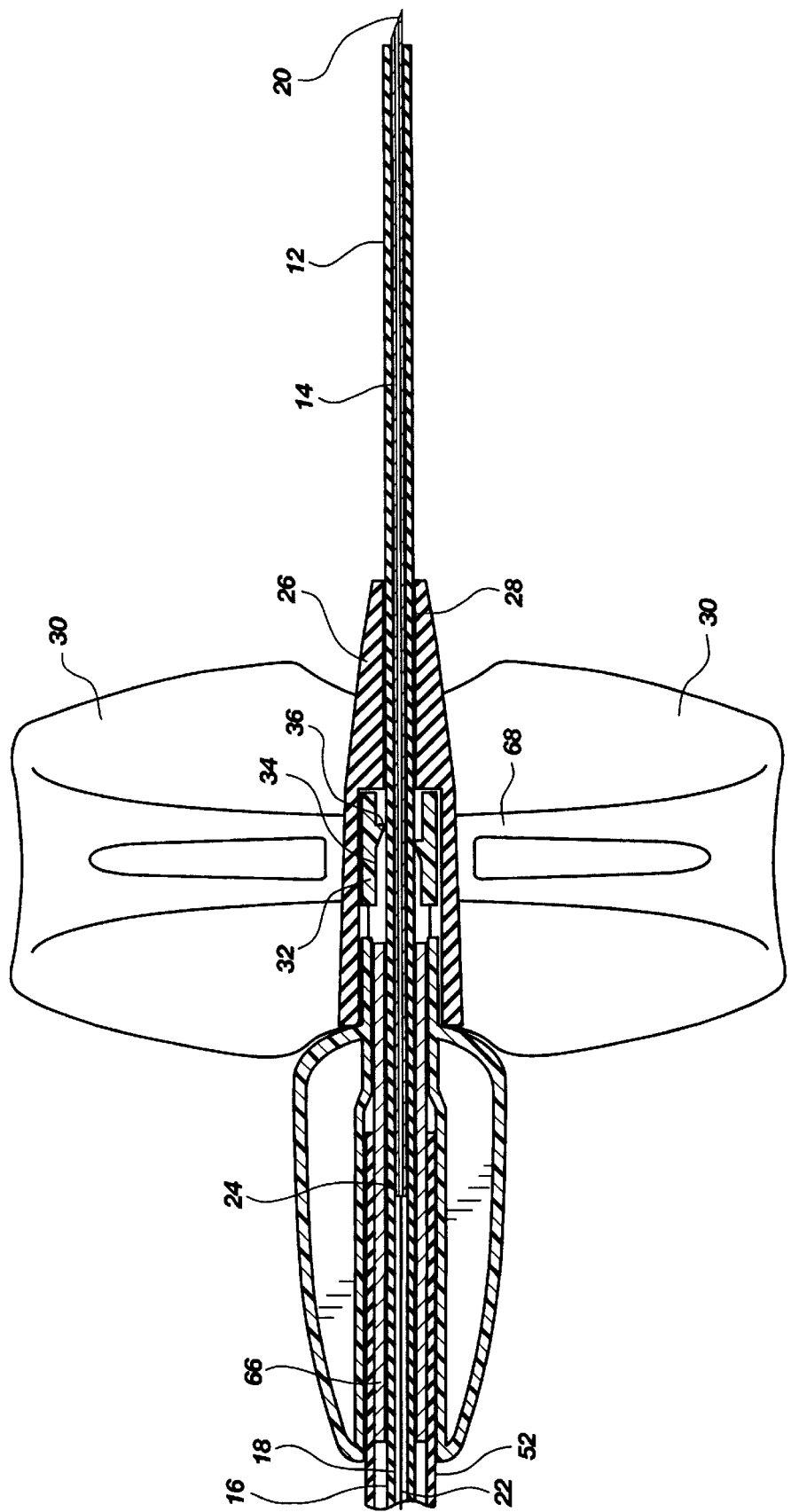
FIG. 3 is an enlarged, longitudinal cross-sectional view of the catheter introducer assembly.
Figure 6:
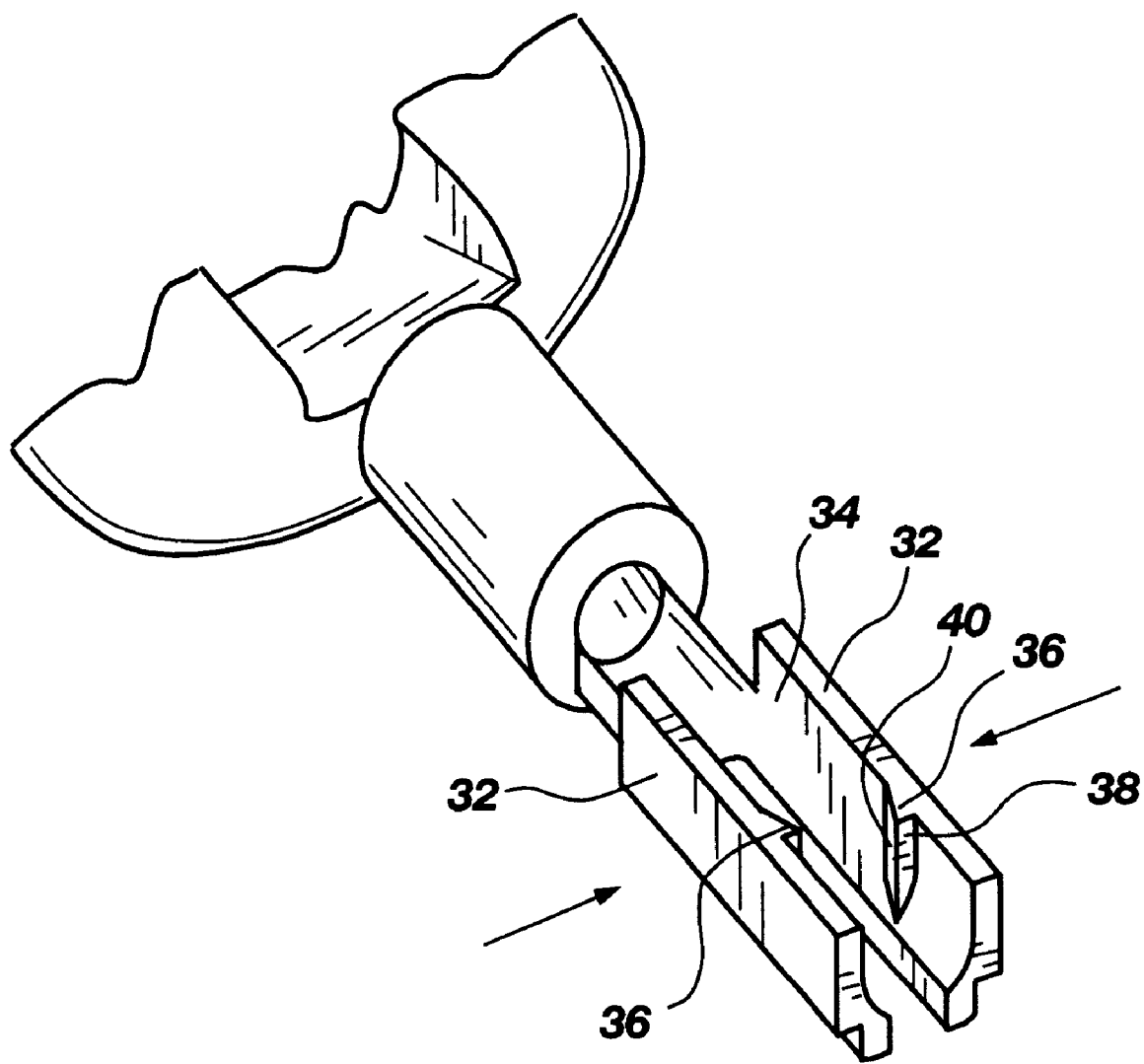
FIG. 6 is an enlarged perspective view of the clamping surfaces within the scope of the present invention.

As shown in FIGS. 3 and 6, the clamp surface ridges 36 are preferably offset so that they do not directly oppose each other. The reason for offsetting the ridges 36 is to provide for improved gripping and to prevent the catheter from being severed by the ridges if an extraordinary gripping force is applied.

In a preferred embodiment, the ridges 36 are sharply tapered on one side of the ridge and gradually tapered on the other side of the ridge. This allows for greater gripping force in one longitudinal direction than another. The sharp taper 38 is preferably on the distal side of the ridge so that the greater gripping force prevents movement of the insertion needle 14 and catheter 12 while the needle and catheter penetrate the patient's skin and blood vessel. The gradual taper 40 is preferably on the proximal side of the ridge to facilitate insertion of the catheter 12.

The insertion needle 14 is preferably hollow, having a sharp beveled tip 20 at its distal end. In a currently preferred embodiment, the needle 14 has a roughened exterior surface to facilitate gripping contact between the interior surface 16 of the catheter 12 and the exterior surface of the needle 14. Sandblasting is one useful method of roughening the needle surface. The needle can also be configured to allow blood flashback to flow through the needle to provide a visual indication of blood vessel penetration. Structures for providing blood flashback are known in the art, such as those described in U.S. Pat. No. 5,385,554.

After the needle 14 and catheter 12 have penetrated a suitable blood vessel, the needle 14 is removed by pulling on the needle handle 46. A receptacle 48 is preferably provided for holding the used needle and preventing exposure of the used needle to the medical practitioner. The needle handle 46 and receptacle 48 are then removed from a catheter hub 50 located at the proximal end of catheter 12. The hub 50 is configured to be connected to a conventional medicament or fluid source. Standard luer connections are currently preferred.

In one preferred embodiment within the scope of the present invention, shown in FIG. 1, the catheter assembly includes a splittable sheath 52 to facilitate insertion of the catheter 12 into the patient. The sheath 52 extends from the hub 50 to a sheath lock 54. The distal end 56 of sheath 52 passes through the sheath lock 54. Both the sheath 52 and catheter 12 are attached to hub 50.

In use, the medical practitioner prepares a site on the patient where the catheter is to be inserted. The apparatus is inspected to be sure the sharp beveled tip 20 is upright. The wings 30 are grasped between the thumb and forefinger, as shown in FIG. 5. When the wings 30 are pinched firmly together, the clamp jaws 32 grip and stabilize the catheter 12 and needle 14. The practitioner performs the venipuncture. The wings 30 are released to the relaxed position, as shown in FIG. 4. The needle 14 is withdrawn by carefully pulling the wire 22.

The catheter 12 is advanced to a desired distance into the patient by pulling the sheath distal end 56. The sheath 52 splits as it passes through the sheath lock 54. When approximately 5 cm of catheter 12 has been advanced into the vein, the catheter 12 is aspirated to remove any air from the system and flushed to assure patency. The catheter 12 is further advanced to a desired location. Once the catheter is properly positioned, the sheath 52 is engaged in the sheath lock 54 to prevent movement of the sheath and catheter 12. Excess sheath 52 can be trimmed. A proximal sheath band 58 is provided at the proximal end of the sheath 52 to prevent the catheter 12 from being advanced too far into the patient. A similar band 60 is located at the distal end of the sheath 52.

FIG. 2 illustrates the various parts assembled to form the catheter introducer assembly. A metal sleeve 66 is disposed within the sheath lock 54. Sleeve 66 is sized such that the catheter 12 and needle 14 fit within the sleeve 66, while the sleeve itself fits within sheath 52. The sleeve 66 protects the catheter 12 from stresses involved in splitting the sheath 52. It also aids in splitting the sheath 52.

Also shown in FIG. 2 are a pair of wedges 68 molded into the surface structure of wings 30. The wedges 68 impinge on the clamp jaws 32 surrounding the catheter 12 and needle 14 when the wings 30 are brought towards each other, as shown in FIG. 5. The wedges 68 enhance the compressive force exerted by wings 30 in the compressed position.

It will be appreciated that the present invention provides a winged catheter introducer which securely clamps and stabilizes the needle and catheter when the wings are pinched.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

What is claimed is:

1. A catheter introducer comprising:
   an introducer body having an introducer lumen extending therethrough;
   a pair of wings attached to said body and extending generally laterally outwardly from said body; and
   at least one clamp jaw disposed within said lumen in abutting relationship to at least a portion of the introducer body that abuts at least one wing and configured such that it moves into engagement with and retains a catheter within the lumen when the wings are compressed together.

2. A catheter introducer according to claim 1, comprising at least two opposing clamp jaws.

3. A catheter introducer according to claim 1, wherein the clamp jaw includes a clamp surface having at least one ridge which engages a catheter positioned within the lumen.

4. A catheter introducer comprising:
   a catheter for introduction into a blood vessel, said catheter having a catheter lumen defining a catheter exterior surface and a catheter interior surface;
   a needle comprising a sharp tip, said needle being partially disposed within the catheter lumen;
   an introducer body having an introducer lumen extending therethrough and having a pair of wings extending from opposite sides of said body, wherein the catheter and needle are disposed within said introducer lumen and wherein said wings are deformable from a relaxed position, where said wings extend substantially laterally from said body, to a compressed position, where said wings are pinched together; and
   a pair of opposing clamp jaws disposed within the introducer lumen in abutting relationship to at least a portion of the introducer body that abuts the wings, wherein said clamp jaws are configured to grip and retain the catheter and needle when the wings are in the compressed position.

5. A catheter introducer according to claim 4, wherein the clamp jaws are biased in an open configuration when the wings are in the relaxed position.

6. A catheter introducer according to claim 4, wherein the clamp jaws each comprise a clamp surface which engages the catheter exterior surface.

7. A catheter introducer according to claim 6, wherein each clamp surface contains at least one ridge which engages the catheter exterior surface.

8. A catheter introducer according to claim 7, wherein the clamp surface ridges transversely engage the catheter exterior surface.

9. A catheter introducer according to claim 7, wherein the clamp surface ridges are sharply tapered on one side of the ridge and gradually tapered on the other side of the ridge.

10. A catheter introducer according to claim 7, wherein the clamp surface ridges are offset and do not directly oppose each other.

11. A catheter introducer according to claim 4, wherein the needle is hollow, having a sharp beveled tip at a distal end thereof and a wire affixed to a proximal end thereof, and wherein the catheter sheathes the needle and wire, except at the beveled tip.

12. A catheter introducer according to claim 4, wherein the needle has a roughened exterior surface to facilitate gripping contact between the interior surface of the catheter and the exterior surface of the needle.

13. A catheter introducer according to claim 4, wherein the needle is configured to allow blood flashback to flow through the needle to provide a visual indication of blood vessel penetration.

14. A catheter introducer comprising:
   a flexible catheter for introduction into a blood vessel, said catheter having a catheter lumen defining a catheter exterior surface and a catheter interior surface;
   a hollow needle disposed within the catheter lumen, said needle comprising a sharp beveled tip at a distal end thereof and a wire affixed to a proximal end thereof, and wherein the catheter lumen sheathes the needle and wire, except at the beveled tip needle, and wherein the needle is configured to allow blood flashback to flow through the needle to provide a visual indication of blood vessel penetration;
   an introducer body having an introducer lumen extending therethrough and having a pair of wings extending from opposite sides of said body, wherein the catheter and needle are disposed within said introducer lumen and wherein said wings are deformable from a relaxed position, where said wings extend substantially laterally from said body, to a compressed position, where said wings are pinched together; and
   a pair of opposing clamp jaws disposed within the introducer lumen in abutting relationship to at least a portion of the introducer body that abuts the wings, wherein each of said clamp jaws has a clamp surface containing at least one angled ridge configured to engage the catheter exterior surface when the wings are in the compressed position, and wherein said clamp jaws are biased in an open configuration when the wings are in the relaxed position.

15. A catheter introducer according to claim 14, wherein the clamp surface ridges transversely engage the catheter exterior surface.

16. A catheter introducer according to claim 14, wherein the clamp surface ridges do not oppose each other.

17. A catheter introducer according to claim 14, wherein the clamp surface ridges are sharply tapered on one side of the ridge and gradually tapered on the other side of the ridge.

18. A catheter introducer according to claim 14, wherein the needle has a roughened exterior surface to facilitate gripping contact between the interior surface of the catheter and the exterior surface of the needle.

* * * * *